(12) United States Patent
Amineh et al.

(10) Patent No.: US 10,605,720 B2
(45) Date of Patent: Mar. 31, 2020

(54) ALIGNMENT OF RESPONSES FOR THICKNESS ESTIMATIONS IN A CORROSION DETECTION TOOL

(71) Applicant: Halliburton Energy Services, Inc., Houston, TX (US)

(72) Inventors: Reza Khalaj Amineh, Houston, TX (US); Burkay Donderici, Houston, TX (US); Luis San Martin, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/060,870

(22) PCT Filed: Jan. 31, 2017

(86) PCT No.: PCT/US2017/015844
§ 371 (c)(1),
(2) Date: Jun. 8, 2018

(87) PCT Pub. No.: WO2018/143947
PCT Pub. Date: Aug. 9, 2018

(65) Prior Publication Data
US 2019/0086321 A1    Mar. 21, 2019

(51) Int. Cl.
*E21B 47/12* (2012.01)
*G01N 17/04* (2006.01)
(Continued)

(52) U.S. Cl.
CPC ......... *G01N 17/04* (2013.01); *E21B 47/0905* (2013.01); *G01N 17/006* (2013.01); *G01N 27/9033* (2013.01); *G01N 27/904* (2013.01)

(58) Field of Classification Search
CPC .... E21B 47/0005; E21B 47/00; E21B 47/082; E21B 47/0905; E21B 47/0006;
(Continued)

(56) References Cited

U.S. PATENT DOCUMENTS

| | | | | |
|---|---|---|---|---|
| 6,561,032 B1* | 5/2003 | Hunaidi | ................ | G01B 17/02 |
| | | | | 702/171 |
| 2009/0195244 A1* | 8/2009 | Mouget | .................... | G01V 3/28 |
| | | | | 324/221 |

(Continued)

FOREIGN PATENT DOCUMENTS

WO    2017196371    5/2016

OTHER PUBLICATIONS

International Search Report and Written Opinion for Application No. PCT/US2017/015844 dated Oct. 31, 2017.
(Continued)

*Primary Examiner* — Alesa Allgood
(74) *Attorney, Agent, or Firm* — Benjamin Fite; C. Tumey Law Group PLLC

(57) ABSTRACT

Systems and methods for corrosion detection of downhole tubulars. A method may comprise disposing a corrosion detection tool in a wellbore, wherein the wellbore comprises a plurality of concentric pipes, wherein the corrosion detection tool comprises: a primary array section comprising a primary array transmitter and primary array receivers; and a high resolution array section comprising a high resolution array transmitter and high resolution array receivers; making a measurement with the primary array section to obtain primary array measurements; making a measurement with the high resolution array section to obtain high resolution array measurements; equalizing resolutions of the primary array section and the high resolution array section; calculating an offset using cross-correlation between the primary
(Continued)

array measurements; shifting the primary array measurements or the high resolution array measurements using the offset to provide shifted data; and performing an inversion on the shifted data to calculate thicknesses of one or more of the concentric pipes.

20 Claims, 13 Drawing Sheets

(51) Int. Cl.
    *E21B 47/09*    (2012.01)
    *G01N 17/00*    (2006.01)
    *G01N 27/90*    (2006.01)

(58) Field of Classification Search
    CPC . E21B 47/12; G01V 1/44; G01V 1/40; G01N 17/02; G01N 2291/02863
    See application file for complete search history.

(56) References Cited

U.S. PATENT DOCUMENTS

| | | |
|---|---|---|
| 2010/0206064 A1 | 8/2010 | Estes |
| 2012/0095686 A1 | 4/2012 | Legendre et al. |
| 2016/0154134 A1 | 6/2016 | Donderici et al. |
| 2016/0187523 A1* | 6/2016 | Sanmartin ............... E21B 47/00 324/339 |
| 2016/0245779 A1 | 8/2016 | Khalaj Amineh et al. |

OTHER PUBLICATIONS

J. Garcia et al., "Successful application of a new electromagnetic corrosion tool for well integrity evaluation in old wells completed with reduced diameter tubular," IPTC 16997. Presented in Beijing, China on Mar. 26-28, 2013.

A. A. Arbuzov et al., "Memory magnetic imaging defectoscopy," SPE 162054. Presented in Moscow, Russia on Oct. 16-18, 2012.

* cited by examiner

ALIGNMENT OF RESPONSES FOR THICKNESS ESTIMATIONS IN A CORROSION DETECTION TOOL

BACKGROUND

For oil and gas exploration and production, a network of wells, installations and other conduits may be established by connecting sections of metal pipe together. For example, a well installation may be completed, in part, by lowering multiple sections of metal pipe (e.g., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, and corrosion transfer, among others. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data may be interpreted to correlate a level of flux leakage or EM induction with corrosion. When multiple casing strings are employed together, correctly managing corrosion detection EM logging tool operations and data interpretation may be complex.

BRIEF DESCRIPTION OF THE DRAWINGS

These drawings illustrate certain aspects of some examples of the present disclosure, and should not be used to limit or define the disclosure.

DETAILED DESCRIPTION

Figure 1:
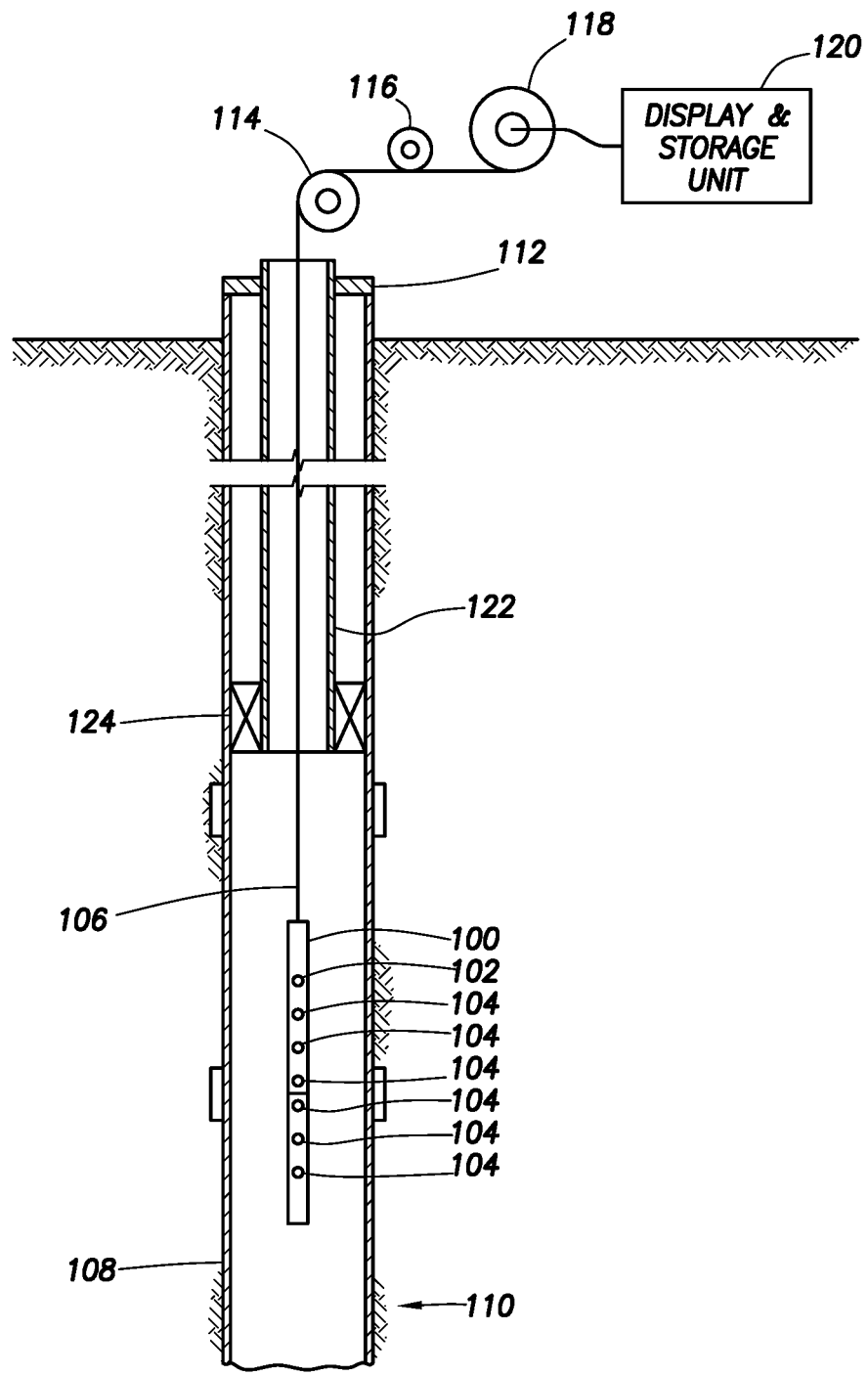
FIG. 1 is a schematic illustration of an example operating environment for a corrosion detection tool.

This disclosure may generally relate to systems and methods for corrosion detection of downhole tubulars, for example, such as casing and pipes (e.g., casing string, a plurality of concentric pipes). This disclosure may relate to Eddy current techniques for multiple pipe characterizations.

Monitoring the condition of the production tubing and possibly multiple casing strings may be crucial in oil and gas field operations. Electromagnetic (EM) techniques are common in inspection of these components. EM techniques may consist of two broad categories: (1) techniques based on the magnetic flux leakage (MFL) and (2) techniques based on Eddy current (EC). While MFL techniques are more suitable for single pipe inspections, EC techniques allow for the multiple pipes characterizations. EC techniques may be divided into two categories, frequency-domain EC techniques and time-domain EC techniques.

In frequency-domain EC techniques, a transmitter (e.g., a transmitter coil) may be fed by a continuous sinusoidal signal, producing primary fields that may illuminate the pipes. The primary fields may produce Eddy currents in the pipes. These Eddy currents, in turn, may produce secondary fields that may be sensed along with the primary fields in the receiver (e.g., receiver coils) that may be placed at a distance from the transmitter. Characterization of the pipes may be performed by measuring and processing these fields.

In time-domain EC techniques (also referred to as pulsed EC (PEC)), the transmitter may be fed by a pulse. Similar to the frequency-domain technique, transient primary fields may be produced due to the transition of the pulse from "off" to "on" state or from "on" to "off" state (more common). These transient fields may produce Eddy currents in the pipes. The Eddy currents may then produce secondary magnetic fields that may be measured by either a separate receiver placed further away from the transmitter, a separate receiver co-located with the transmitter, or the same receiver that was used as the transmitter.

In an inversion scheme for multiple pipe inspection, a 1D (one-dimensional) radial model may be employed to expedite the process. The inversion scheme may comprise a one-dimensional algorithm. The responses of each section of the corrosion detection tool may be aligned along a depth of a wellbore so that all the responses may correspond to the same depth. Then, the pipe parameters may be estimated at that depth. However, while applying this alignment of the receivers along the depth, the corrosion detection tool misplacement during the logging due to sticks and slips may produce errors. If the distance between the receivers is short, this error may be negligible, but this misalignment error may lead to large errors if the distance between the receivers is large.

To acquire stronger responses from outer pipes, typically, a longer transmitter may be employed together with larger receivers that may be placed at large distances from the transmitter (i.e., some receivers may be placed at large distances from the transmitter). This section of the corrosion detection tool may be the primary array ("PA"). In the PA section, the receivers may be placed at distances of about 30 inches or more from the transmitter. The transmitters and/or receivers in PA section may have any suitable frequency range, including, from about 0.5 Hertz ("Hz") to about 8 Hz. However, measurements with these large receivers and larger transmitter-receiver distances may degrade the vertical (along the depth) resolution in the thickness estimation results. To achieve better resolution, smaller receivers with shorter transmitter-receiver distances and measurement at higher frequencies may be employed to perform thickness estimation of inner pipes with higher vertical resolution. This section of the corrosion detection tool may be the high resolution array ("HRA"). In the HRA section, the receivers may be placed at distances of about 30 inches or less from the transmitters. The transmitters and/or receivers in HRA section may have any suitable frequency range, including, from about 12 Hertz ("Hz") to about 48 Hz. In both the PA section and the HRA section, any suitable transmitters and receivers may be used. Suitable transmitters may include transmitter coils or solenoidal windings. Suitable receivers may include receiver coils or solenoidal windings. In addition, the transmitters and receivers used in the PA section may be longer and spaced farther than the receivers used in the HRA section. For example, in the case of coil transmitters and receivers, the transmitters and receivers in the PA section may be separated by distances that range from 10 inches to 180 inches with a length of 2 inches to 50 inches. The HR section transmitters and receivers may be separated by distances that range from 2 inches to 50 inches (5.1 cm to 127 cm), and with a length of 0.5 inch to 20 inches (1.3 cm to 50.8 cm). The ratio of the smallest spacing of PA to smallest spacing of HR may be larger than 2. The ratio of the length of the smallest coil of PA to smallest coil of HR may be larger than 2.

FIG. 1 illustrates an operating environment for a corrosion detection tool 100 as disclosed herein. Corrosion detection tool 100 may comprise transmitter 102 and receivers 104. Corrosion detection tool 100 may be operatively coupled to a conveyance line 106 (e.g., wireline, slickline, coiled tubing, pipe, or the like) which may provide mechanical suspension, as well as electrical connectivity, for corrosion detection tool 100. Conveyance line 106 and corrosion detection tool 100 may extend within casing string 108 to a desired depth within the wellbore 110. Conveyance line 106, which may include one or more electrical conductors, may exit wellhead 112, may pass around pulley 114, may engage odometer 116, and may be reeled onto winch 118, which may be employed to raise and lower the corrosion detection tool 100 in the wellbore 110. Signals recorded by corrosion detection tool 100 may be stored on memory and then processed by display and storage unit 120 after recovery of corrosion detection tool 100 from wellbore 110. Alternatively, signals recorded by corrosion detection tool 100 may be conducted to display and storage unit 120 by way of conveyance line 106. Display and storage unit 120 may process the signals, and the information contained therein may be displayed for an operator to observe and stored for future processing and reference. Display and storage unit 120 may also contain an apparatus for supplying control signals and power to the downhole tool assembly, wherein the downhole tool assembly comprises corrosion detection tool 100. A typical casing string 108 may extend from wellhead 112 at or above ground level to a selected depth within a wellbore 110. Casing string 108 may comprise a plurality of joints or segments of casing, each segment being connected to the adjacent segments by a threaded collar.

FIG. 1 also illustrates a typical pipe string 122, which may be positioned inside of casing string 108 extending part of the distance down wellbore 110. Pipe string 122 may be production tubing, tubing string, casing string, or other pipe disposed within casing string 108. Pipe string 122 may include concentric pipes. A packer 124 typically may seal the lower end of the tubing-casing annulus and may secure the lower end of the pipe string 122 to the casing. The corrosion detection tool 100 may be dimensioned so that it may be lowered into the wellbore 110 through the pipe string 122, thus avoiding the difficulty and expense associated with pulling the pipe string 122 out of the wellbore 110.

In logging systems, such as, for example, logging systems utilizing the corrosion detection tool 100, a digital telemetry system may be employed, wherein an electrical circuit may be used to both supply power to the corrosion detection tool 100 and to transfer data between display and storage unit 120 and corrosion detection tool 100. A DC voltage may be provided to the corrosion detection tool 100 by a power supply located above ground level, and data may be coupled to the DC power conductor by a baseband current pulse system. Alternatively, the corrosion detection tool 100 may be powered by batteries located within the downhole tool assembly, and/or the data provided by the corrosion detection tool 100 may be stored within the downhole tool assembly, rather than transmitted to the surface during logging (e.g., corrosion detection).

Transmission of electromagnetic fields by the transmitter 102 and the recordation of signals by the receivers 104 may be controlled by an information handling system. Systems and methods of the present disclosure may be implemented, at least in part, with an information handling system. An information handling system may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 2:
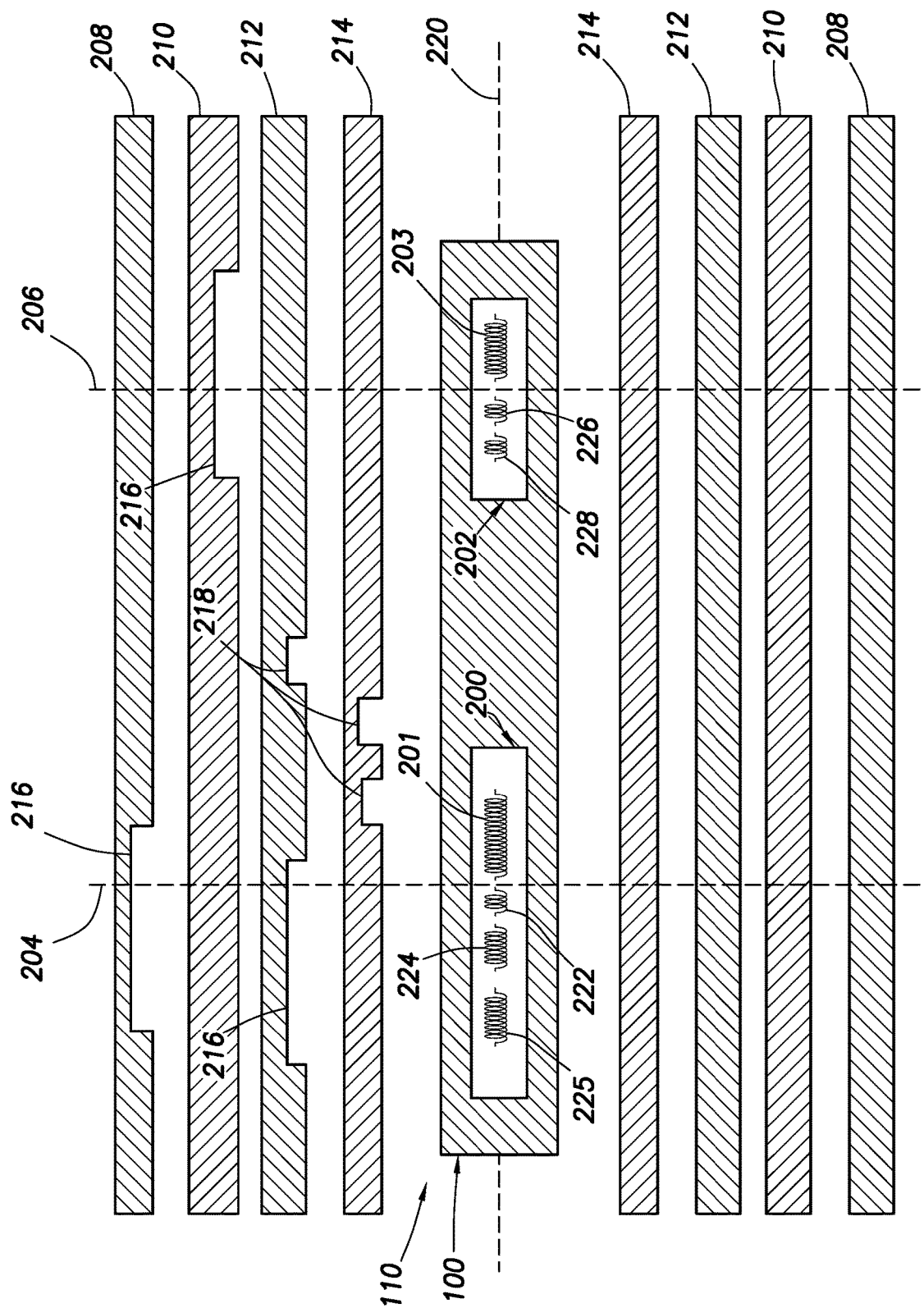
FIG. 2 is a schematic illustration of an example corrosion detection tool in which different depth of penetration and also vertical resolution may be achieved via separate sections.

FIG. 2 illustrates corrosion detection tool 100 in which different depths of penetration and vertical resolution may be achieved via separate sections (e.g., PA section 200 and HRA section 202). As illustrated, corrosion detection tool 100 is disposed in wellbore 110. Corrosion detection tool 100 may include PA section 200 and HRA section 202 with alignment lines 204 and 206, respectively. Measurements may be made with PA section 200 to obtain primary array measurements. Measurements may be made with HRA section 202 to obtain high resolution array measurements. Alignment line 204 illustrates the position of the effective measurement point of the PA section 200. Alignment line 206 illustrates the position of the effective measurement point of the HRA section 202. Here effective measurement point is the position at which half of the sensitive volume of the tool is before the point, and half of the sensitive volume of the tool is after the point. Effective measurement point is typically close to the middle point between the center of the transmitter coil and the center of the receiver coil. In most cases it can be chosen equal to the middle point. Different transmitter receiver pairs may have different effective measurement points. The effective measurement point of HR and PA may be aligned through depth shifting to obtain responses that peak roughly at the same depth. PA section 200 may include PA transmitter 201 and PA receivers 222, 224, 225. The PA receivers 222, 224, 225 may be referred to herein collectively as PA receivers 222, 224, 225 and individually as first PA receiver 222, second PA receiver 224, and third PA receiver 225. HRA section 202 may include HRA transmitters 203 and HR receivers 226, 228. The HR receivers 226, 228 may be referred to collectively as HR receivers 226, 228, and individually as first HR receiver 226 and second HR receiver 228. The HRA section 202, when compared to the PA section 200, may employ shorter coils for the HRA transmitter 203 and the HRA receivers 226, 228, as well as shorter transmitter-receiver distances, and higher frequencies to characterize the defects (e.g., small defects 218) on the inner pipes (e.g., inner pipes 212, 214) only. Processing these responses from the HRA section 202 leads to high vertical resolution in characterization of inner pipes 212, 214. The primary array (PA), when compared to the HRA, employs longer TX and RX coils, longer TX-RX distances, and lower frequencies to measure responses due to both inner pipes and outer pipes (e.g., outer pipes 208, 210). Processing these responses may lead to lower vertical resolution in characterization of inner pipes but may provide characterization of outer pipes as well.

In wellbore 110, corrosion detection tool 100 may be positioned between a plurality of concentric pipes, shown as outer pipes 208, 210 and inner pipes 212, 214. Defects may be present in one or more of outer pipes 208, 210 and inner pipes 212, 214. The defects may include corrosion, perforations, collars, chokes, valves or any other downhole device. As illustrated, large defects 216 may be positioned, for example, on outer pipes 208, 210 and inner pipe 212. Small defects 218 may be positioned, for example, on inner pipes 212 and 214. The responses of all the PA receivers 222, 224, 225 and HRA receiver 226, 228 may be aligned along alignment line 220. Then, a 1D radial model may be employed to estimate the pipe parameters corresponding to the depth at which the alignment lines 200 and 202 pass.

As described above, large errors in the thickness estimation may result if the distance (i.e., offset) between the alignment lines 204 and 206 for PA section 200 and HRA section 202, respectively, is large. The primary array measurements or the high resolution array measurements may be shifted using the offset to provide shifted data. An offset of about 6 inches (15.2 cm) or more may be considered large for first pipe thickness estimation with a small first pipe diameter, for example. For pipe diameters that are large, or for deeper pipes, 12-24 inches (30.5-71 cm) may be considered large. Large may refer to an appearance of inversion or processing artifacts that result from the misalignment in integration of PA and HRA. Various methods may be employed to integrate the PA and HRA inversion processing. The responses may be inverted to pipe parameters separately or they may be combined in a single inversion processing scheme. In the former case, proper alignment (i.e., equalizing resolutions of the PA and the HRA) of the inversion results may be required along the depth so that the estimated thickness results may correspond to the same depth for both sections (e.g., PA section 200 and HRA section 202). In the latter case, proper alignment of the responses along the depth may be required, so that the responses from both sections (e.g., PA section 200 and HRA section 202) may correspond to the same depth before applying the inversion algorithm.

If the positioning of corrosion detection tool 100 is perfect, i.e. tool logs with an even speed along the depth, the alignment of the responses or the thickness estimation results may have been straight-forward from the known positions of transmitters (e.g., PA transmitter 201 and HRA transmitter 203) and receivers (e.g., PA receivers 222, 224, 225 and HRA receivers 226, 228) and the dimensions of corrosion detection tool 100. However, the uncertainty in positioning of the corrosion detection tool 100 during the logging procedure due to inevitable sticks and slips may require a more reliable processing algorithm to implement the alignment of the responses prior to applying the inversion algorithm or aligning the thickness estimation results after applying the inversion algorithm.

One technique may include alignment of responses for the PA section 200. As previously described, PA section 200 may comprise PA receivers 222, 224, 225 that may be placed at various distances from the PA transmitter 201. The large variation in the position of the PA receivers 222, 224, 225 may makes this section prone to errors due to misalignment of the responses in real-life logging procedures where the velocity of corrosion detection tool 100 is non-uniform. To align the responses: 1) For each receiver response and at each frequency, deconvolution may be applied to reduce the effect of the size of the PA transmitter 201 and PA receivers 222, 224, 225 and the transmitter-receiver distance. Applying deconvolution on the responses may be implemented practically using a method described below; 2) By selecting one receiver in the PA section 200, e.g., first PA receiver 222 (RX1) as the reference receiver, the alignment distances $\bar{z}_i$s (i.e., offsets) for other the other receivers RXi (e.g., second PA receiver 224 and third PA receiver 225) may be estimated as follows:

$$\bar{z}_i = \underset{\bar{z}}{\mathrm{argmax}}(\mathrm{corr}(R_1(z, f), R_i(z, f))(\bar{z})) \quad (1)$$

where $R_1(z, f)$ and $R_i(z, f)$ are the normalized deconvolved responses of the reference receiver RX1 and RXi along the depth z and at frequency f, respectively. Each response can be normalized to its maximum absolute value. corr(*,*) may be the cross-correlation operation defined as:

$$\mathrm{corr}(R_1(z,f),R_i(z,f))(\bar{z}) = \int R_1^*(z,f) R_i(z+\bar{z},f) dz \quad (2)$$

Once the alignment distances $\bar{z}_i$s are estimated for all the receivers (except first PA receiver 222 which was assumed to be the reference receiver), the responses of the receivers (e.g., PA receivers 222, 224, 225) may be shifted along the depth by the corresponding distances and then are fed to the 1D inversion algorithm to estimate the thickness at the corresponding aligned depth.

Figure 3:
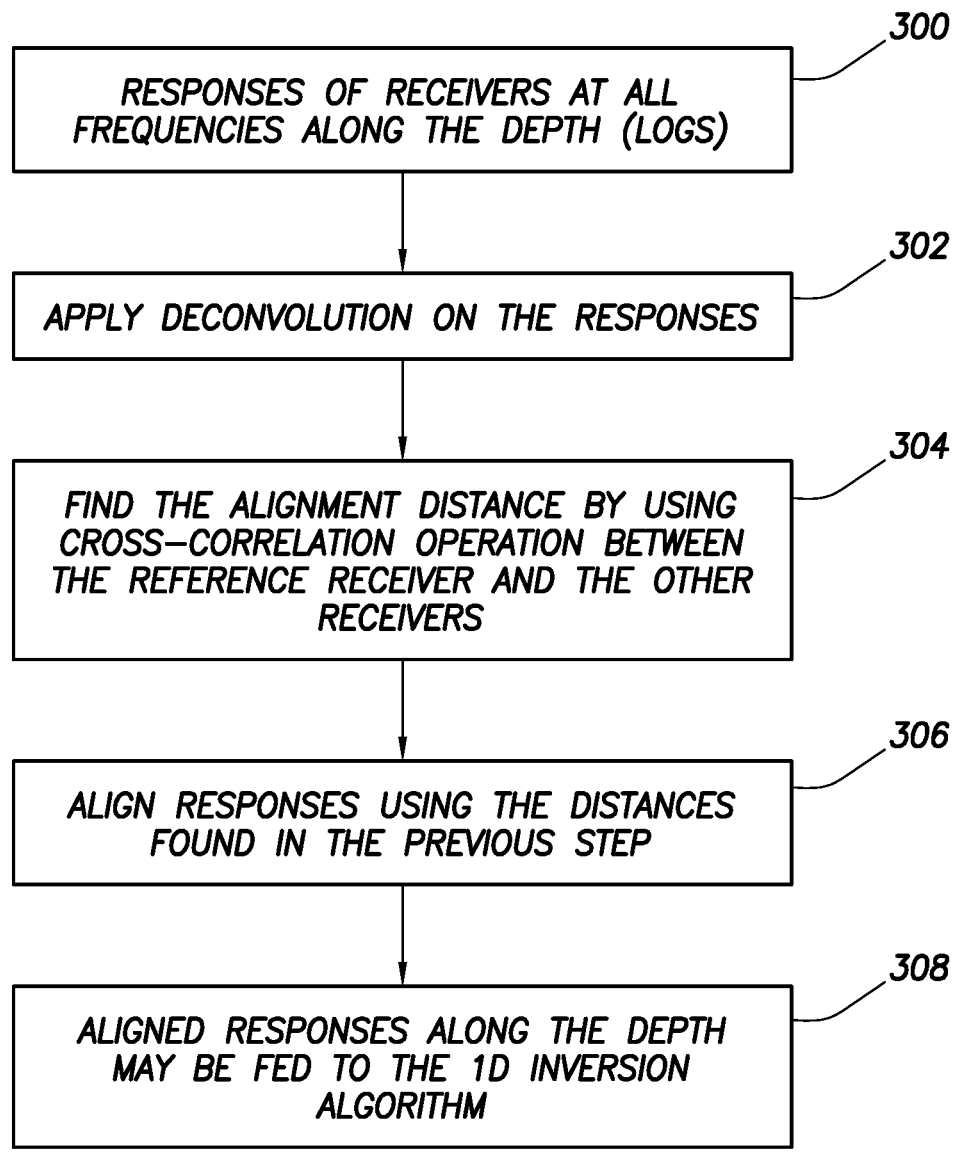
FIG. 3 illustrates an example of a flowchart implementing alignment along the depth for the responses acquired by a primary array ("PA") section of a corrosion detection tool.

FIG. 3 illustrates a flowchart implementing alignment along the depth for the responses acquired by the PA section 200 of the corrosion detection tool 100. Box 300 shows responses of receivers (e.g., receivers 222, 224, 225, 226 and 228) at all frequencies along the depth (logs). Box 302 shows applying deconvolution on the responses. Box 304 shows finding the alignment distance (i.e., offset) by using a cross-correlation operation between the reference receiver (e.g., receiver 222) and the other receivers (e.g., receivers 224, 225, 226 and 228). Box 306 shows aligning responses using distances found in box 304 (previous step). Box 308 shows that the aligned responses along the depth may be fed to the 1D inversion algorithm.

Alternatively, another technique may include alignment of responses between PA section 200 and HRA section 202. It may be assumed that the responses of the PA section 200 and HRA section 202 may be aligned accurately among themselves using the corrosion detection tool 100 dimensions and assuming uniform velocity for the corrosion detection tool 100. But the distance between the PA section 200 and HRA section 202 is large such that if the responses of both sections are simultaneously fed to a 1D inversion algorithm, the aligned responses of the PA section 200 should be aligned properly with the aligned response of HRA section 202 (assuming uniform velocity may lead to errors in practice). It may be assumed that the PA section 200 and HRA section 202 have at least one receiver that is placed at approximately the same distance from its corresponding transmitter (for example, first PA receiver 222 and first HRA receiver 226 in FIG. 2). Also, it may be assumed that both PA section 200 and HRA section 202 acquire responses in at least one similar measurement frequency f.

The responses of the PA receivers 222, 224, 225) and HRA receivers 226, 228) may be first aligned for each section separately without any further processing. The aligned responses of PA section 200 may be referred to as the responses of PA section 200 and the aligned responses of HRA section 202 may be referred to as the responses of HRA section 202. Then, the goal may be to align the responses of the PA (for a subset or all the PA receivers 222, 224, 225) with the responses of the HRA (for a subset or all the HRA receivers 226, 228).

It may be assumed that first PA receiver 222 (RX1) in PA section 200 is placed at a similar distance from PA transmitter 201 as first HRA receiver 226 (RX1) in HRA section 202 with its corresponding HRA transmitter 203. Then, the alignment distance $\bar{z}_0$ (i.e., offset) between the two sections may be estimated as:

$$\bar{z}_0 = \underset{\bar{z}}{\mathrm{argmax}}(\mathrm{corr}(R_1^{PA}(z,f), R_1^{HRA}(z,f))(\bar{z})) \quad (3)$$

where $R_1^{PA}(z, f)$ and $R_1^{HRA}(z, f)$ may be the normalized responses of the first PA receiver 222 and first HRA receiver 226 along the depth z and at frequency f respectively. Each response may be normalized to its maximum absolute value along the depth. corr(*,*) is the cross-correlation operation defined as:

$$\mathrm{corr}(R_1^{PA}(z,f), R_1^{HRA}(z,f))(\bar{z}) = \int R_1^{PA*}(z,f) R_1^{HRA}(z+\bar{z}, f) dz \quad (4)$$

Once the alignment distance $\bar{z}_0$ is estimated between the PA section 200 and HRA section 202, it may be used to align the responses of the PA section 200 with the responses of HRA section 202. The aligned responses may then be fed to a 1D inversion algorithm to estimate the thickness of the pipes at the corresponding depth.

Figure 4:
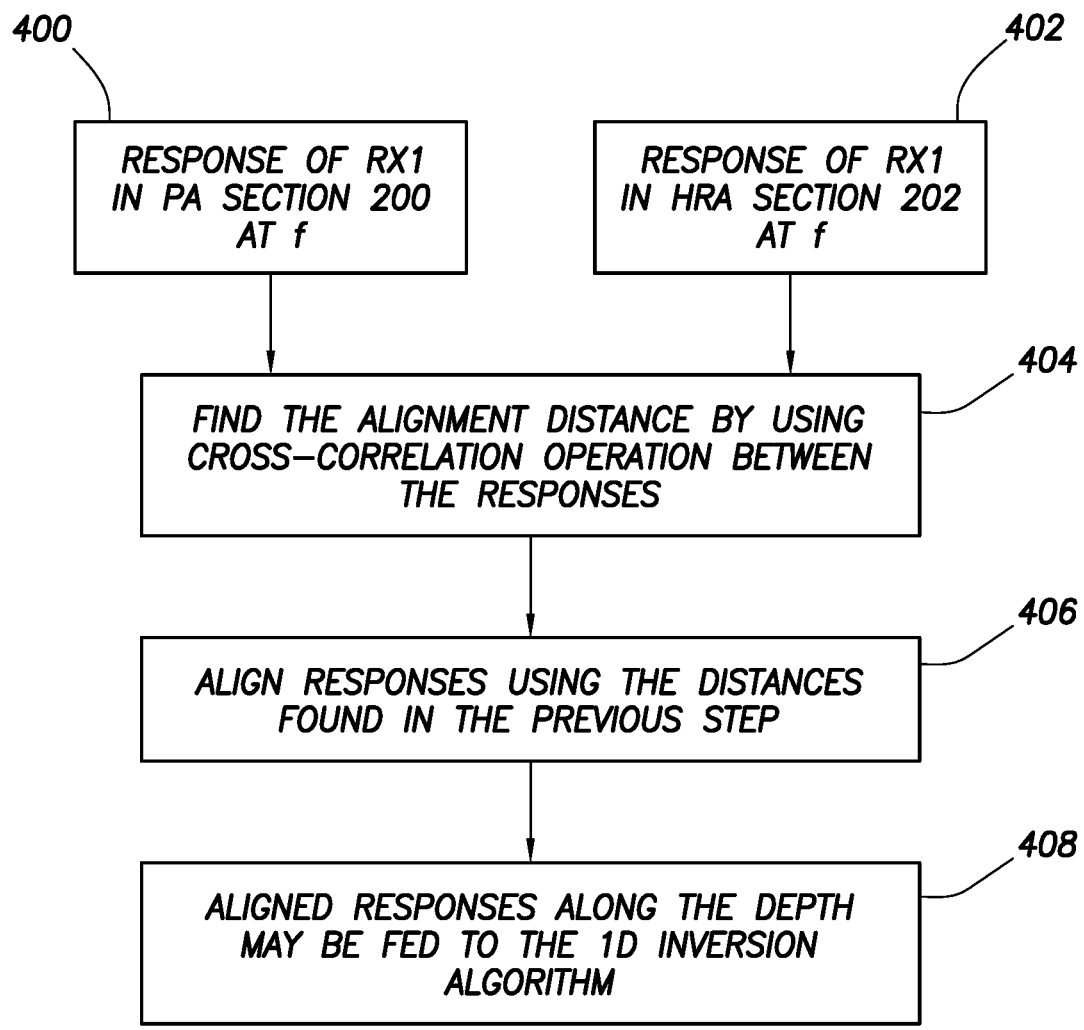
FIGS. 4 and 5 illustrate example flowcharts implementing alignment along the depth for the responses acquired by the PA primary array and high resolution array ("HRA") sections.

FIG. 4 illustrates a flowchart of implementing alignment along the depth for the responses acquired by the PA section 200 and HRA section 202, assuming that first PA receiver 222 and first HRA receiver 226 are placed at similar distances with respect to their transmitters (e.g., PA transmitter 201 and HRA transmitter 203) and may perform measurements at a similar frequency f Box 400 shows a response of first PA receiver 225 (RX1 in PA section 200 at f). Box 402 shows a response of first HRA receiver 226 (RX1 in HRA section 202 at f). Box 404 shows finding the alignment distance (i.e., offset) by using a cross-correlation operation between the responses. Box 406 shows aligning the responses using the distances found in box 404 (previous step). Box 408 shows that the aligned responses along the depth may be fed to the 1D inversion algorithm.

It may alternatively be assumed that PA section 200 and HRA section 202 do not have receivers (e.g., PA receivers 222, 224, 225 and HRA receivers 226, 228) that are placed at similar distances from their corresponding transmitter (e.g., PA transmitters 201 and HRA transmitters 203) but may acquire responses in at least one similar frequency f. Then, to align the responses: 1) For at least one PA receiver response and at least one HRA receiver response, and at the common frequency f, apply deconvolution to reduce the effect of the size of the transmitters and receivers and the transmitter-receiver distances by techniques described herein; 2) The alignment distance $\bar{z}_0$ between the PA and HRA responses may be estimated from the cross-correlation between the normalized deconvolved PA and HRA responses (for example, $R_1^{PA}(z, f)$ and $R_1^{HRA}(z, f)$ similar to the previous step 1). Once the alignment distance $\bar{z}_0$ is estimated between the PA section 200 and HRA section 202, it may be used to align the responses of the PA section 200 with the responses of HRA section 202. The aligned responses may then be fed to a 1D inversion algorithm to estimate the thickness of the pipes at the corresponding depth.

Figure 5:
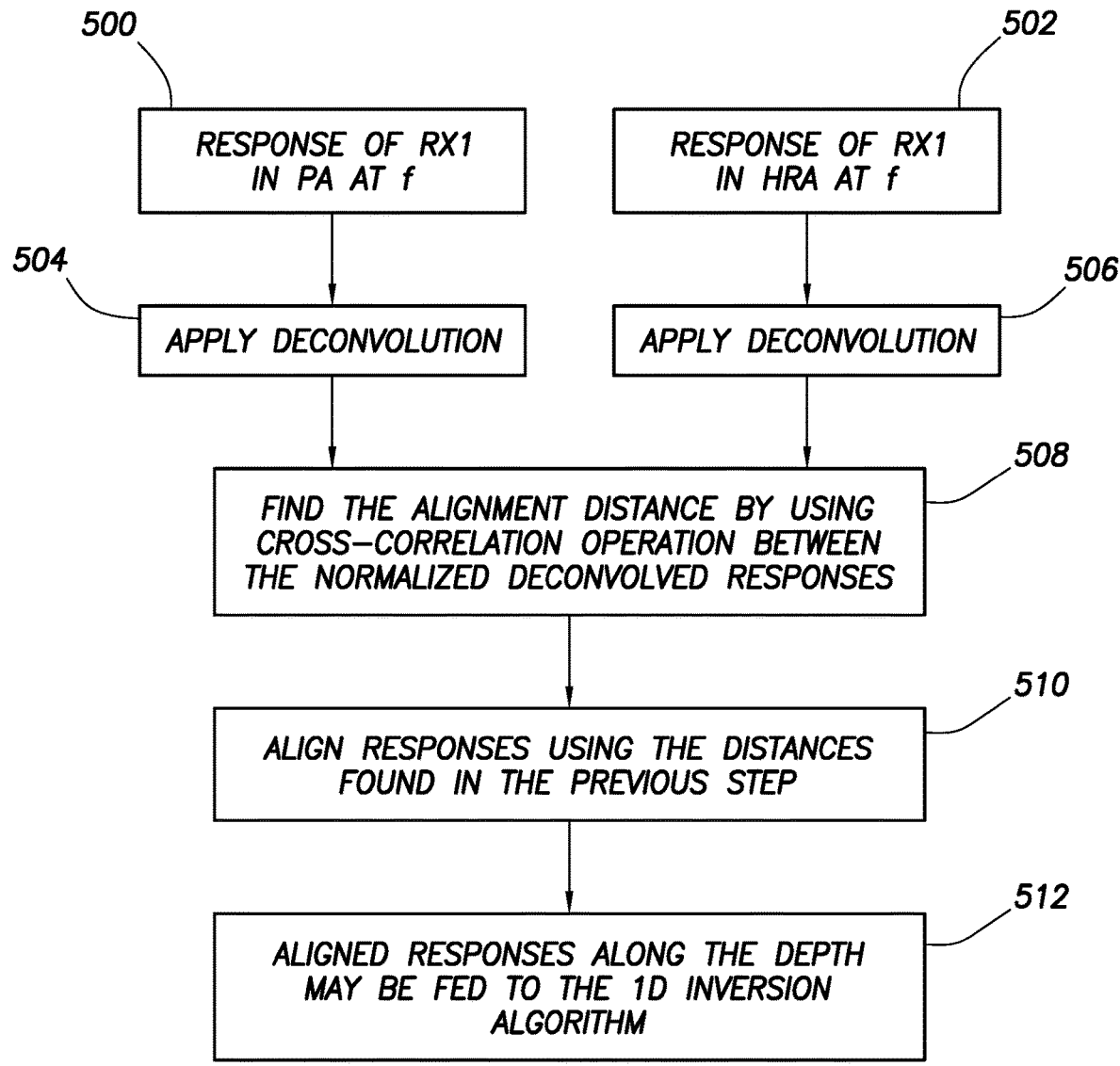

FIG. 5 illustrates a flowchart of implementing alignment along the depth for the responses acquired by the PA section 200 and HRA section 202, assuming that first PA receiver 222 (RX1 in PA section 200) and receiver 226 (RX1 in HRA section 202) are placed at different distances with respect to their transmitters (e.g., PA transmitter 201 and HRA transmitter 203) but they perform measurement at a similar frequency f.

Alignment of the thickness estimations for the PA section 200 and HRA section 202 when they are fed to separate 1D inversion algorithms: the alignment techniques described above may be applied on the responses of PA section 200 and HRA section 202 to estimate the alignment distance $\bar{z}_0$ between the two sections. This alignment distance may then be employed to shift the estimated thicknesses along the depth for the PA section 200 and HRA section 202 to produce accurate estimations of the thickness along the depth from both sections.

Figure 6:
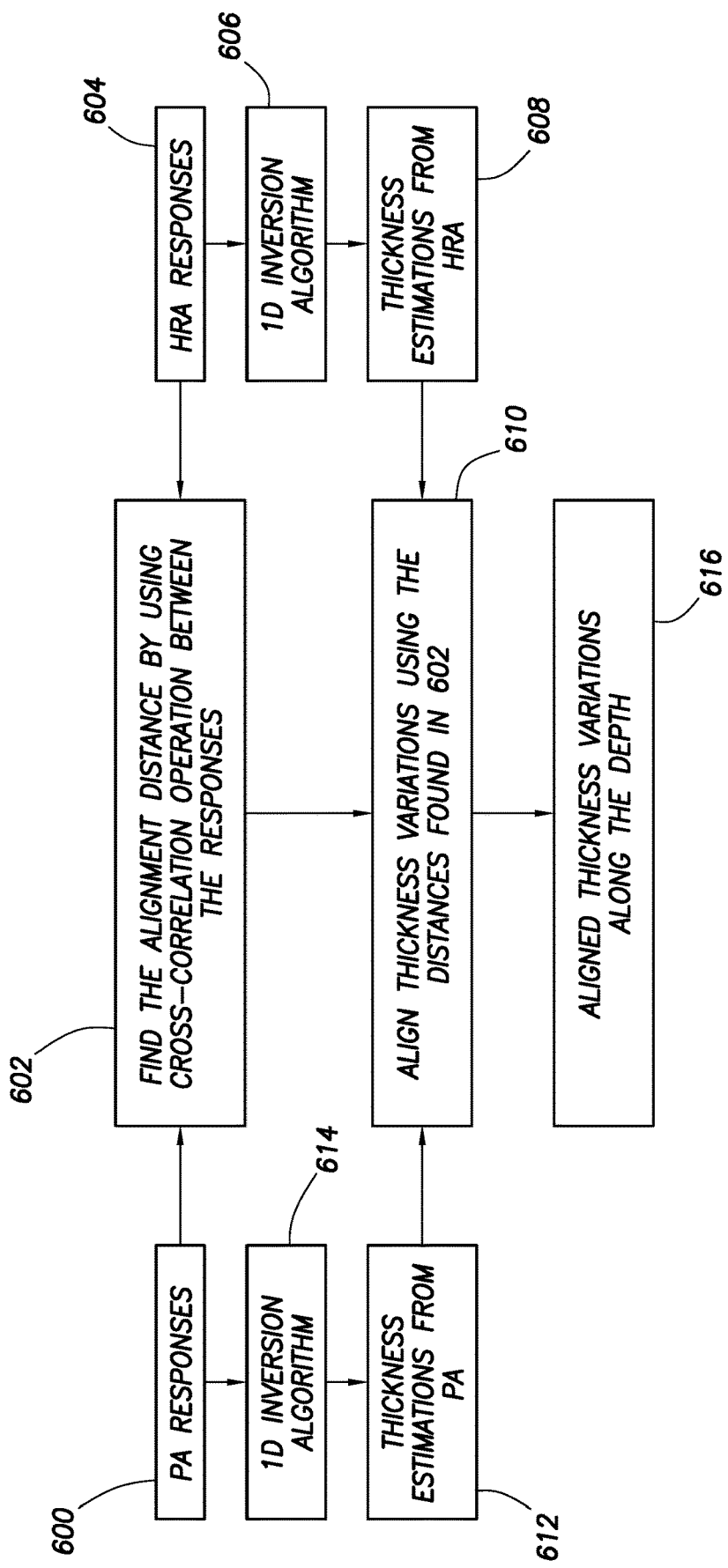
FIG. 6 illustrates an example flow chart implementing alignment along the depth for the thickness estimations obtained from PA and HRA inversion algorithms.

FIG. 6 illustrates a flowchart of implementing alignment along the depth for the thickness estimations obtained from PA and HRA inversion algorithms. To find the alignment distance, one of the techniques described above may be applied to the PA and HRA responses. Box 600 shows PA responses. Box 602 shows finding the alignment distance by using a cross-correlation operation between the responses using above-mentioned techniques. Box 604 shows HRA responses. Box 606 shows a 1D inversion algorithm. Box 608 shows thickness estimations from HRA. Box 610 shows aligning thickness variations using the distances found in box 602 (previous step). Box 612 shows thickness estimations from PA. Box 614 shows a 1D inversion algorithm. Box 616 shows aligned thickness variations along the depth.

A cross-correlation operation may be applied on the estimated thickness variations (on at least one of the pipes) obtained from PA section 200 and HRA section 202. The estimated thickness variations from PA section 200 and HRA section 202 for the first pipe (e.g., inner pipe 212 on FIG. 2) may be denoted by $T_1^{PA}(z)$ and $T_1^{HRA}(z)$, respectively. Then, the alignment distance may be estimated directly from the cross-correlation between $T_1^{PA}(z)$ and $T_1^{HRA}(z)$. For a better alignment, this cross-correlation may be computed after applying a proper processing method such as deconvolution on the thickness estimations as: 1) Apply deconvolution on the thickness estimations $T_1^{PA}(z)$ and $T_1^{HRA}(z)$ using aforementioned techniques; 2) The alignment distance $\overline{z}_0$ between the PA and HRA thickness estimations may be estimated from the cross-correlation between the deconvolved PA and HRA thickness estimations.

Figure 7:
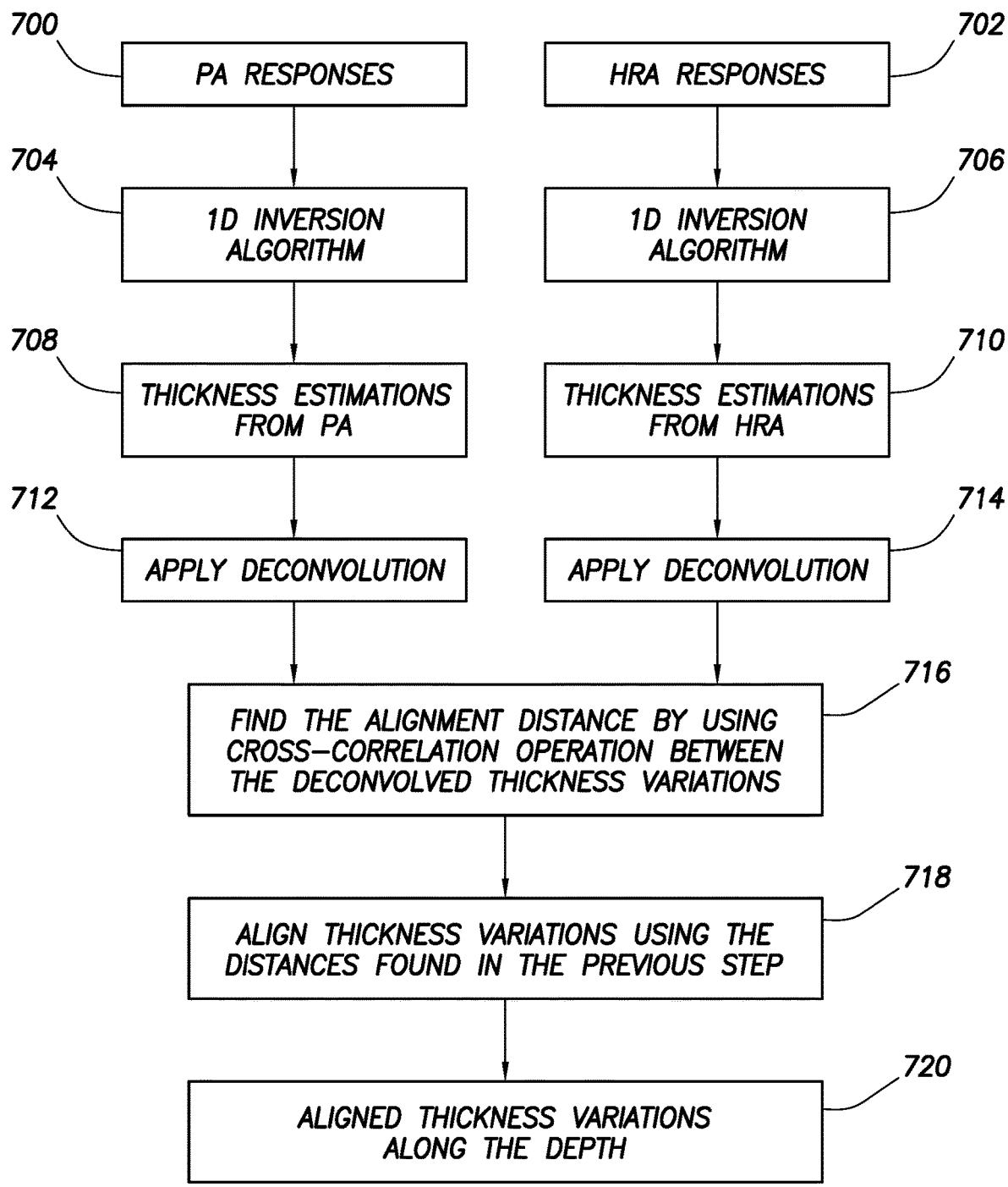
FIG. 7 illustrates another example flow chart implementing alignment along the depth for the thickness estimations obtained from PA and HRA inversion algorithms.

FIG. 7 shows a flowchart of implementing alignment along the depth for the thickness estimations obtained from PA and HRA inversion algorithms. To find the alignment distance, deconvolution may be applied to the thickness variations of one pipe, for both PA and HRA inversion results, to reduce the effects of coil sizes and transmitter-receiver distances. Box 700 shows PA responses. Box 702 shows HRA responses. Boxes 704 and 706 show 1D inversion algorithms. Boxes 708 and 710 show thickness estimations from PA section 200 and HRA section 202. Boxes 712 and 714 show applying deconvolutions. Box 716 shows finding the alignment distance by using a cross-correlation operation between the deconvolved thickness variations. Box 718 shows aligning thickness variations using the distances found in box 716 (previous step). Box 720 shows the aligned thickness variations along the depth.

An example is now described showing improvement that may be obtained through the alignment of the HRA section 202 and PA section 200 when thickness estimation results for these two sections are utilized. Table 1 shows the parameters of three pipes (i.e., pipe 1, pipe 2, pipe 3) being inspected in this example. This table also shows the parameters of the defects placed on these pipes.

Figure 8:
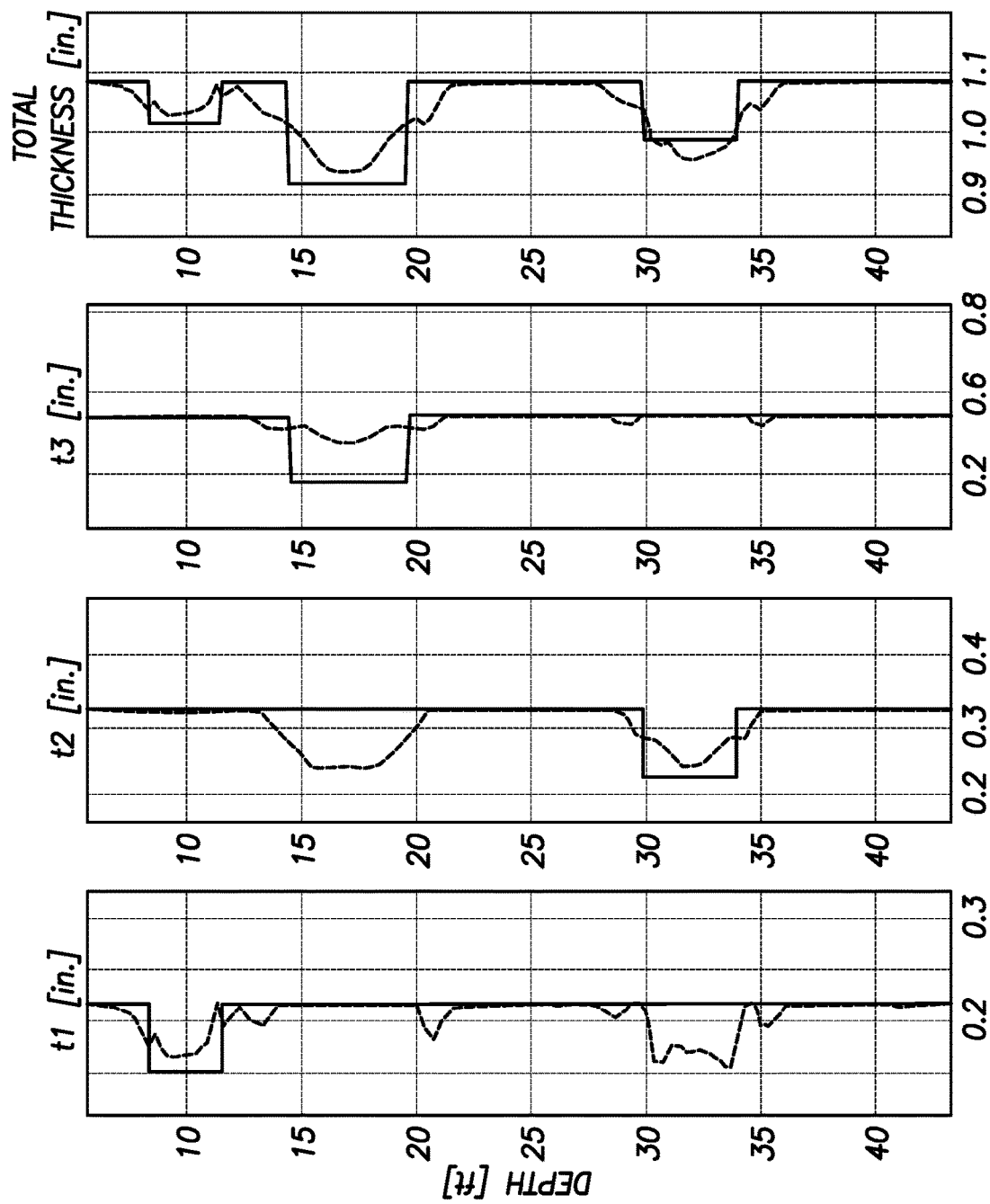
FIGS. 8 and 9 illustrate example graphs showing thickness estimation results for the data obtained from the PA section.

FIG. 8 shows the thickness estimation results when the data acquired by PA 200 in the frequency range of about 0.5 to about 8 Hz and an inversion technique may be employed to estimate the thickness variation of these three pipes (i.e., pipe 1, pipe 2, and pipe 3). It may be observed that although the overall thickness estimation for the pipes (sum of thickness values for all the pipes) may be acceptable, the thickness estimation for individual pipes may show large errors for all the pipes.

Figure 9:
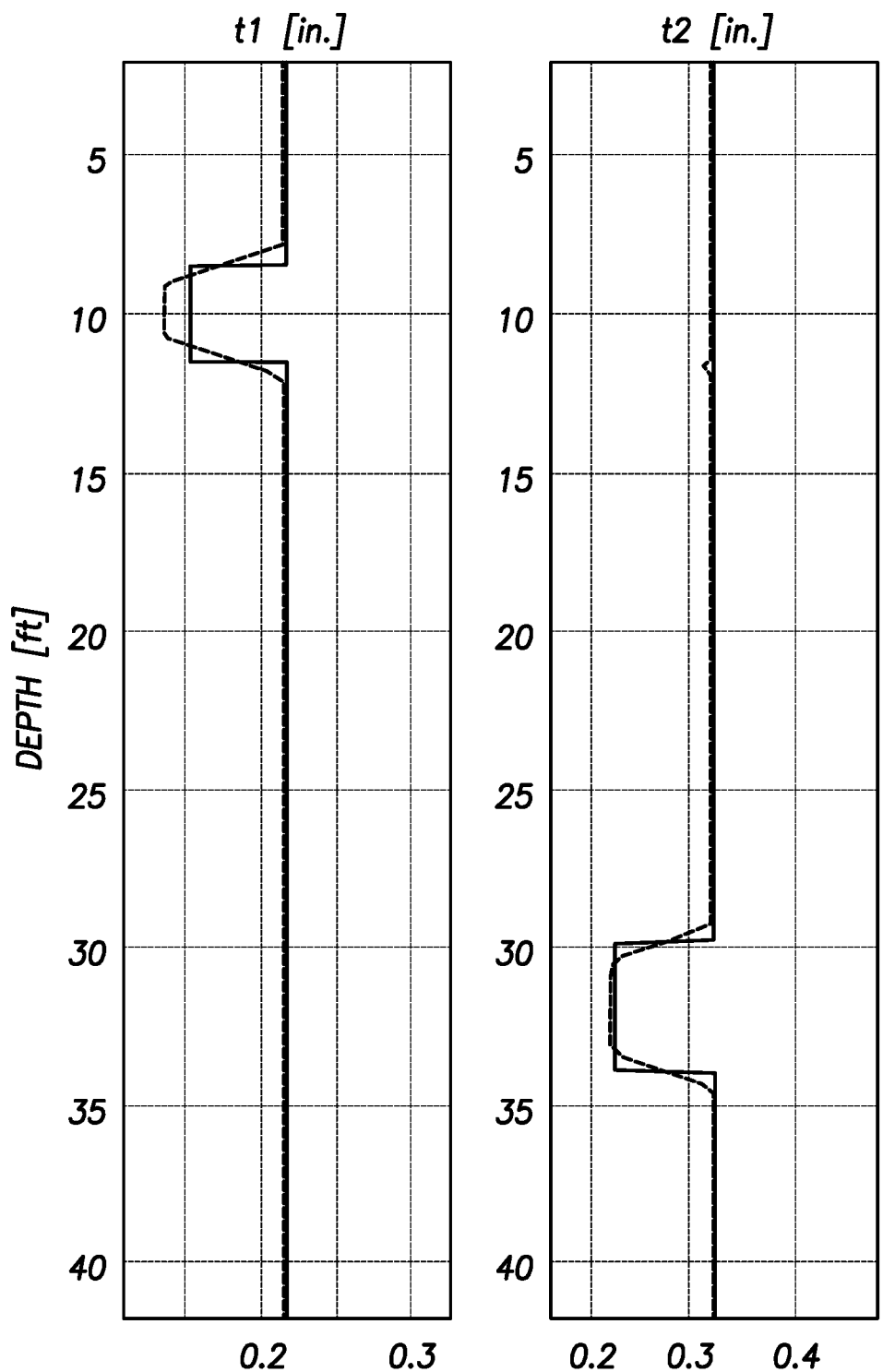

To improve the thickness estimation results, an inversion may be performed on the data obtained from HRA section 202 for pipes 1 and 2. FIG. 9 shows the estimated thickness variations from this step and the data collected in the range of about 12 Hz to about 48 Hz may be utilized. It may be observed that the estimated thickness variations for both pipes may be accurate. These thickness estimation results may be employed and the data obtained from PA section 200 to estimate the thickness variations on pipe 3 (while keeping the thickness variations on pipes 1 and 2 fixed as those obtained from HRA inversion step).

Figure 10:
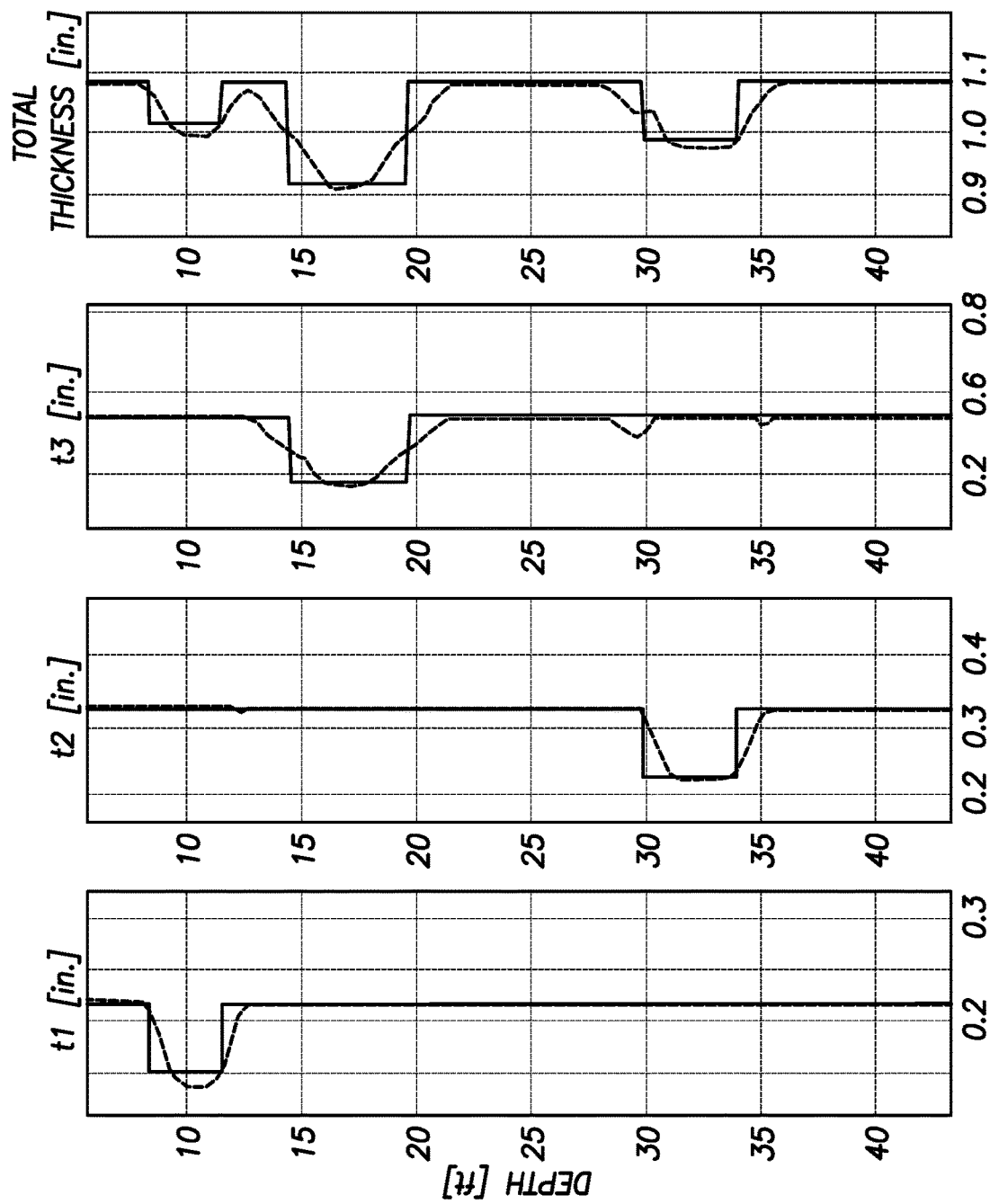
FIGS. 10-13 illustrate examples of graphs showing thickness estimation results when using the inversion results from HRA section for pipes 1 and 2 during the inversion process for PA data to estimate thickness variation on pipe 3.
Figure 11:
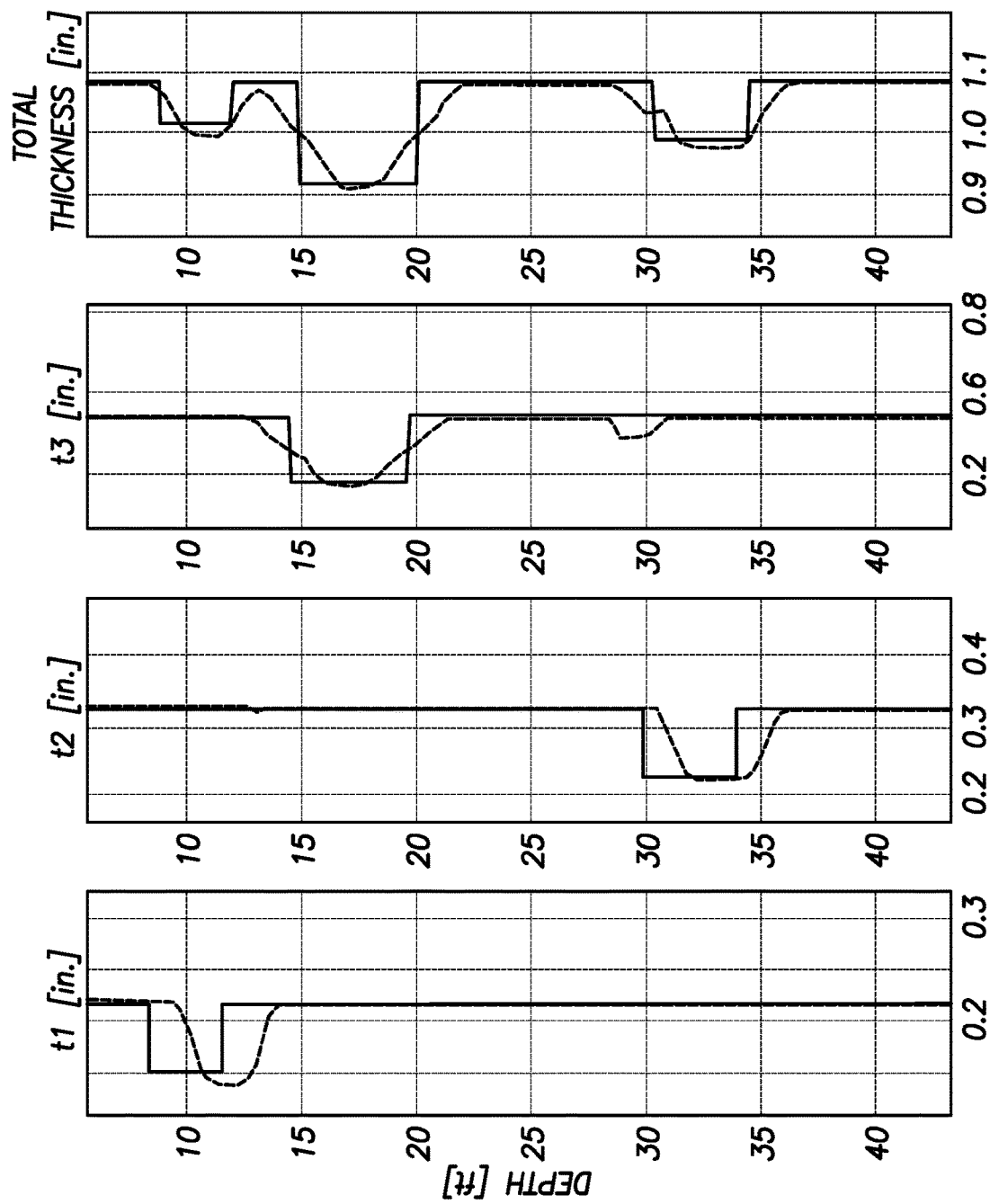
Figure 12:
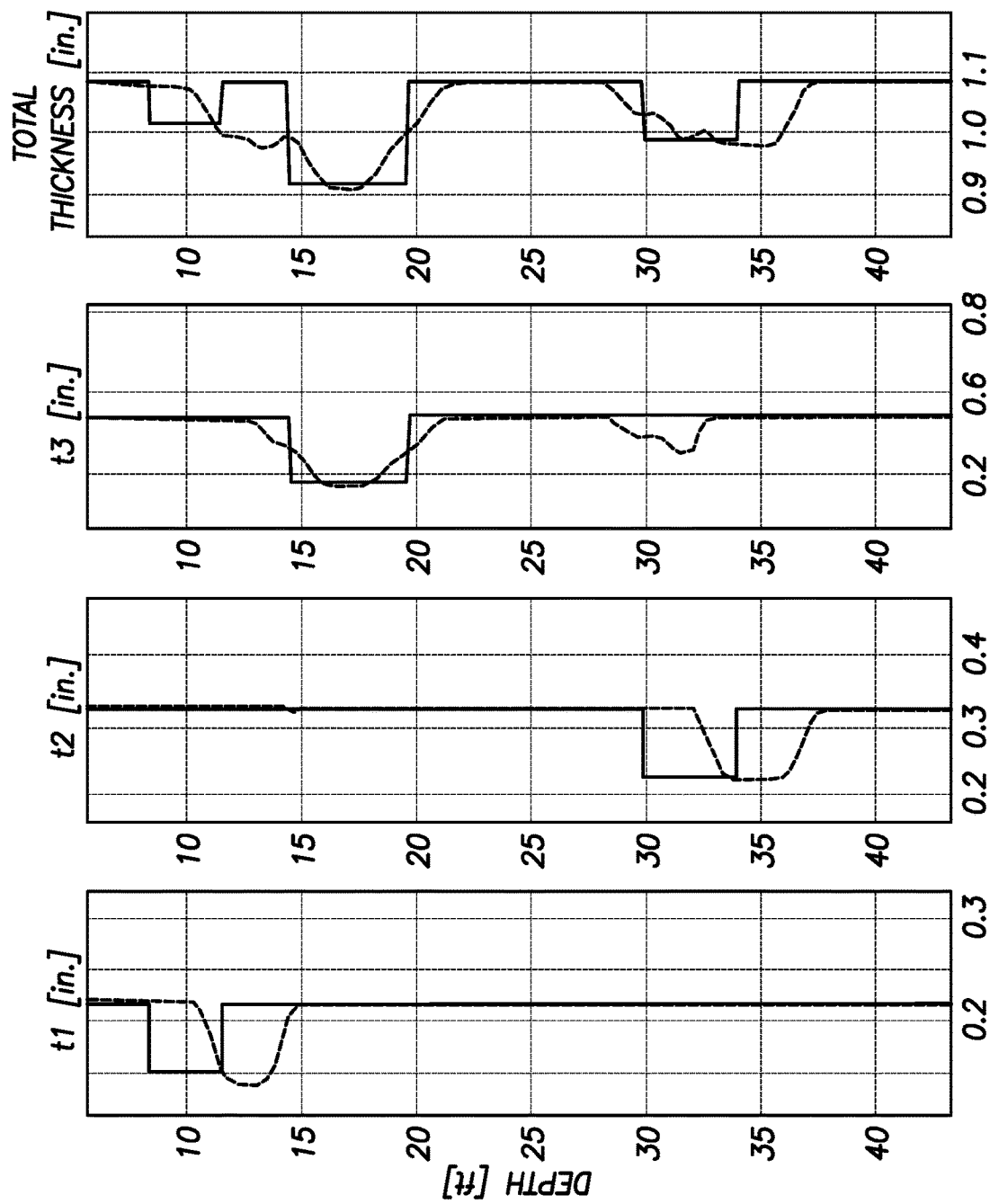
Figure 13:
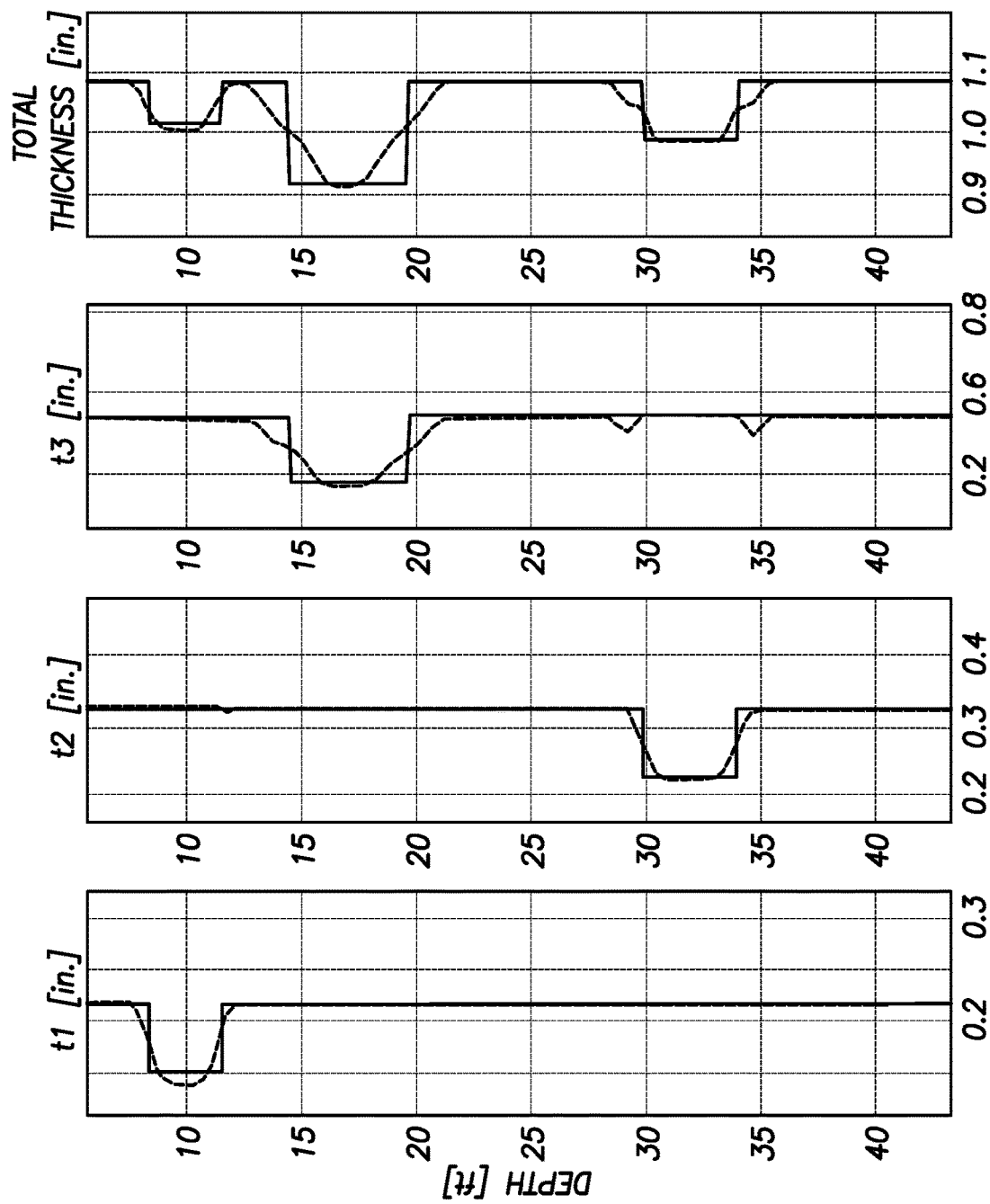

Errors in the alignment of the depth parameters for the PA section 200 and HRA section 202 may be introduced, in this example, assuming that the alignment of the data based on only the recorded depth on the surface is not accurate. Three error values in the depth alignment may be introduced as: 0.5 ft (15 cm), 1.5 ft (46 cm), and 2.5 ft (76 cm). FIGS. 10, 11, and 12 show the thickness estimation results when using the inversion results from HRA section 202 for pipes 1 and 2 and employ data from PA section 200 to estimate the thickness of pipe 3. It may be observed that as the depth alignment error increases from 0.5 ft (15 cm) to 2.5 ft (76 cm), the estimation of the thickness variation for pipe 3 may become more erroneous. This may show the necessity for using a depth alignment approach to correct for this error and improve the thickness estimation results for pipe 3. To perform depth alignment, approaches disclosed above (e.g., computing the cross-correlation between the thickness estimation results from HRA section 202 and PA section 200) to evaluate the depth alignment distance. FIG. 13 shows the thickness estimation results when applying the inversion process on the aligned data. It clearly shows improvement compared to the results shown in FIGS. 10 to 12.

Accordingly, this disclosure describes systems and methods that may be used for corrosion detection of downhole

TABLE 1

Parameters of pipe 1, pipe 2, and pipe 3.

| Pipe No. | Pipe OD | Pipe Thickness | Relative Magnetic Permeability ($\mu_r$) | Electrical Conductivity ($\sigma$) | Defect Size (length × depth) | Defect's Center Depth |
|---|---|---|---|---|---|---|
| 1 | 2⅞ in (7.3 cm) | 0.21 in (0.53 cm) | 5 | $4 \times 10^6$ | 3 in × 0.06 in (7.6 cm × 0.15 cm) | 10 ft (3 m) |
| 2 | 7 in (17.8 cm) | 0.32 in (0.81 cm) | 76 | $4 \times 10^6$ | 4 in × 0.1 in (10.2 cm × 0.25 cm) | 32 ft (9.8 m) |
| 3 | 9⅝ in (24.4 cm) | 0.54 in (1.37 cm) | 76 | $4 \times 10^6$ | 5 in × 0.16 in (12.7 cm × 0.41 cm) | 17 ft (5.2 m) |

To estimate the thickness variations on these pipes, a corrosion detection tool 100 as shown in FIG. 2 may be utilized, for example. For this example, PA section 200 of the corrosion detection tool 100 includes one PA transmitter 201 and six PA receivers 222, 224, 225 (noting that FIG. 2 only shows three PA receivers 222, 224, 225), and the HRA section 202 includes HRA transmitter 203 and three PA receivers 226, 228 (noting that FIG. 2 only shows two HRA receivers 226, 228).

FIG. 8 shows the thickness estimation results when the data acquired by PA 200 in the frequency range of about 0.5 tubulars. Without limitation, the systems and methods may further be characterized by one or more of the following statements:

Statement 1: A method may comprise disposing a corrosion detection tool in a wellbore, wherein the wellbore comprises a plurality of concentric pipes, wherein the corrosion detection tool comprises: a primary array section comprising a primary array transmitter and primary array receivers; and a high resolution array section comprising a high resolution array transmitter and high resolution array receivers; making a measurement with the primary array section to obtain primary array measurements; making a measurement with the high resolution array section to obtain high resolution array measurements; equalizing resolutions of the primary array section and the high resolution array section; calculating an offset using cross-correlation between the primary array measurements; shifting the primary array measurements or the high resolution array measurements using the offset to provide shifted data; and performing an inversion on the shifted data to calculate thicknesses of one or more of the concentric pipes.

Statement 2: The method of Statement 1, wherein the equalizing resolutions comprises aligning responses from the primary array section and responses from the high resolution array section.

Statement 3: The method of Statement 1 or Statement 2, wherein the calculating an offset comprises calculating an alignment distance between the primary array section and the high resolution array section.

Statement 4: The method of any preceding statement, wherein the shifting is performed along a depth of the wellbore.

Statement 5: The method of any preceding statement, wherein the high resolution array section comprises transmitter-receiver distances shorter than transmitter-receiver distances of the primary array section.

Statement 6: The method of any preceding statement, wherein the high resolution array section is configured to employ frequencies which are higher than frequencies of the primary array section.

Statement 7: The method of any preceding statement, wherein the primary array section employs frequencies in a frequency range of about 0.5 Hz to about 8 Hz; wherein the high resolution array section employs frequencies in a frequency range of about 12 Hz to about 48 Hz.

Statement 8: The method of any preceding statement, wherein transmitter-receiver distances in the primary array section are about 30 inches or more.

Statement 9: The method of any preceding statement, wherein transmitter-receiver distances in the primary array section are larger than transmitter-receiver distances in the high resolution array section.

Statement 10: The method of any preceding statement, wherein the primary array section is configured to characterize defects on inner pipes and outer pipes of the concentric pipes.

Statement 11: A corrosion detection system may comprise a corrosion detection tool disposed within a wellbore, wherein the corrosion detection tool comprises: a primary array section comprising a primary array transmitter and primary array receivers; and a high resolution array section comprising a high resolution array transmitter and high resolution array receivers; an information handling system configured to: receive measurements from the primary array section; receive measurements from the high resolution array section; equalize resolutions of the primary array section and the high resolution array section; calculate an offset using cross-correlation between the measurements from primary array measurements; shift the measurements from the primary array section or the measurements from the high resolution array section using the offset to provide shifted data; and perform an inversion on the shifted data to calculate thicknesses of pipes.

Statement 12: The corrosion detection system of Statement 11, wherein the high resolution array section comprises transmitter-receiver distances shorter than transmitter-receiver distances of the primary array section.

Statement 13: The corrosion detection system of Statement 11 or Statement 12, wherein transmitter-receiver distances in the primary array section are about 30 inches or more.

Statement 14: The corrosion detection system of any one of Statements 11 to 13, wherein the primary array section employs frequencies in a frequency range of about 0.5 Hz to about 8 Hz; wherein the high resolution array section employs frequencies in a frequency range of about 12 Hz to about 48 Hz.

Statement 15: The corrosion detection system of any one of Statements 11 to 14, wherein the wellbore comprises a plurality of concentric pipes comprising inner pipes and outer pipes.

Statement 16: The corrosion detection system of any one of Statements 11 to 15, wherein the primary array section is configured to characterize defects on the inner pipes and the outer pipes.

Statement 17: The corrosion detection system of any one of Statements 11 to 16, wherein the inner pipes and the outer pipes comprise various thicknesses.

Statement 18: The corrosion detection system of any one of Statements 11 to 17, wherein the high resolution array section is configured to characterize defects on the inner pipes only.

Statement 19: The corrosion detection system of any one of Statements 11 to 18, wherein the inversion comprises a one-dimensional algorithm.

Statement 20: The corrosion detection system of any one of Statements 11 to 19, wherein the offset comprises an alignment distance between the primary array section and the high resolution array section.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method comprising:
  disposing a corrosion detection tool in a wellbore, wherein the wellbore comprises a plurality of concentric pipes, wherein the corrosion detection tool comprises:
    a primary array section comprising a primary array transmitter and primary array receivers; and
    a high resolution array section comprising a high resolution array transmitter and high resolution array receivers;
  taking a measurement of one or more responses at one or more frequencies with the primary array section to obtain primary array measurements at each of the primary array receivers;
  taking a measurement of the one or more responses at the one or more frequencies with the high resolution array section to obtain high resolution array measurements at each of the high resolution array receivers;
  equalizing resolutions of the primary array section and the high resolution array section;
  selecting one of the primary array receivers as a primary array reference receiver;
  selecting one of the high resolution array receivers as a high resolution reference receiver;
  calculating one or more primary array offsets using cross-correlation between the primary array reference receiver and each of the other receivers in the primary array receivers;
  calculating one or more high resolution offsets using cross-correlation between the high resolution reference receiver and each of the other receivers in the high resolution array receivers;
  shifting the primary array measurements and the high resolution array measurements using the one or more primary array offsets and one or more high resolution offsets to provide shifted data; and
  performing an inversion on the shifted data to calculate thicknesses of one or more of the concentric pipes.

2. The method of claim 1, wherein the equalizing resolutions comprises deconvolving the primary array measurements at each of the primary array receivers and deconvolving the high resolution array measurements at each of the high resolution array receivers.

3. The method of claim 1, further comprising calculating an alignment distance between the primary array section and the high resolution array section.

4. The method of claim 1, wherein the shifting is performed along a depth of the wellbore.

5. The method of claim 1, wherein the high resolution array section comprises transmitter-receiver distances shorter than transmitter-receiver distances of the primary array section.

6. The method of claim 1, wherein transmitter-receiver distances in the primary array section are about 30 inches or more.

7. The method of claim 1, wherein transmitter-receiver distances in the primary array section are larger than transmitter-receiver distances in the high resolution array section.

8. The method of claim 1, wherein the primary array section is configured to characterize defects on inner pipes and outer pipes of the concentric pipes.

9. The method of claim 1, wherein the high resolution array section is configured to employ frequencies which are higher than frequencies of the primary array section.

10. The method of claim 9, wherein the primary array section employs frequencies in a frequency range of about 0.5 Hz to about 8 Hz; wherein the high resolution array section employs frequencies in a frequency range of about 12 Hz to about 48 Hz.

11. A corrosion detection system comprising:
  a corrosion detection tool disposed within a wellbore, wherein the corrosion detection tool comprises:
    a primary array section comprising a primary array transmitter and primary array receivers; and
    a high resolution array section comprising a high resolution array transmitter and high resolution array receivers;
  an information handling system configured to:
    receive measurements of one or more responses at one or more frequency from the primary array section;
    receive measurements of the one or more responses at the one or more frequencies from the high resolution array section;
    equalize resolutions of the primary array section and the high resolution array section;
    select one of the primary array receivers as a primary array reference receiver;
    select one of the high resolution array receivers as a high resolution reference receiver;
    calculate one or more primary array offsets using cross-correlation between the primary array reference receiver and each of the other receivers in the primary array receivers;
    calculate one or more high resolution offsets using cross-correlation between the high resolution reference receiver and each of the other receivers in the high resolution array receivers;
    shift the measurements from the primary array section and the measurements from the high resolution array section using the one or more primary offsets and one or more high resolution offsets to provide shifted data; and
    perform an inversion on the shifted data to calculate thicknesses of pipes.

12. The system of claim 11, wherein the primary array section employs frequencies in a frequency range of about 0.5 Hz to about 8 Hz; wherein the high resolution array section employs frequencies in a frequency range of about 12 Hz to about 48 Hz.

13. The system of claim 11, wherein the inversion comprises a one-dimensional algorithm.

14. The system of claim 11, wherein the offset comprises an alignment distance between the primary array section and the high resolution array section.

15. The system of claim 11, wherein the high resolution array section comprises transmitter-receiver distances shorter than transmitter-receiver distances of the primary array section.

16. The system of claim 15, wherein transmitter-receiver distances in the primary array section are about 30 inches or more.

17. The system of claim 11, wherein the wellbore comprises a plurality of concentric pipes comprising inner pipes and outer pipes.

18. The system of claim 17, wherein the primary array section is configured to characterize defects on the inner pipes and the outer pipes.

19. The system of claim 17, wherein the inner pipes and the outer pipes comprise various thicknesses.

20. The system of claim 19, wherein the high resolution array section is configured to characterize defects on the inner pipes only.

\* \* \* \* \*